US008940701B2

(12) United States Patent
Livant

(10) Patent No.: US 8,940,701 B2
(45) Date of Patent: Jan. 27, 2015

(54) COMPOUNDS FOR, AND METHODS OF, TREATING CANCER AND INHIBITING INVASION AND METASTASES

(75) Inventor: Donna Livant, Ann Arbor, MI (US)

(73) Assignee: The Regents of the University of Michigan, Ann Arbor, MI (US)

(*) Notice: Subject to any disclaimer, the term of this patent is extended or adjusted under 35 U.S.C. 154(b) by 145 days.

(21) Appl. No.: 13/319,476

(22) PCT Filed: May 12, 2010

(86) PCT No.: PCT/US2010/034497
§ 371 (c)(1),
(2), (4) Date: Dec. 9, 2011

(87) PCT Pub. No.: WO2010/132537
PCT Pub. Date: Nov. 18, 2010

(65) Prior Publication Data
US 2012/0077755 A1    Mar. 29, 2012

Related U.S. Application Data

(60) Provisional application No. 61/177,830, filed on May 13, 2009.

(51) Int. Cl.
*A61K 31/337*    (2006.01)
*A61K 38/08*    (2006.01)
*C07K 7/06*    (2006.01)
*A61K 45/06*    (2006.01)

(52) U.S. Cl.
CPC .................. *C07K 7/06* (2013.01); *A61K 31/337* (2013.01); *A61K 38/08* (2013.01); *A61K 45/06* (2013.01)
USPC ........................................................ 514/19.3

(58) Field of Classification Search
None
See application file for complete search history.

(56) References Cited

U.S. PATENT DOCUMENTS

| 3,993,073 | A | 11/1976 | Zaffaroni | 424/424 |
| 5,051,448 | A | 9/1991 | Shashoua | 514/574 |
| 5,169,862 | A | 12/1992 | Burke, Jr. et al. | 514/450 |
| 5,192,746 | A | 3/1993 | Lobl et al. | 514/9.3 |
| 5,539,085 | A | 7/1996 | Bischoff et al. | 530/350 |
| 5,559,103 | A | 9/1996 | Gaeta et al. | 514/54 |
| 5,576,423 | A | 11/1996 | Aversa et al. | 530/388.75 |
| 5,660,848 | A | 8/1997 | Moo-Young | 424/425 |
| 6,001,965 | A | 12/1999 | Livant | 530/330 |
| 2006/0078535 | A1 | 4/2006 | Livant | 424/78.27 |

FOREIGN PATENT DOCUMENTS

| WO | WO 98/22617 | * | 5/1998 |
| WO | WO9822617 A1 | | 5/1998 |
| WO | WO2006084016 A1 | | 8/2006 |

OTHER PUBLICATIONS

Livant et al., Cancer Res., 2000, 60: 309-320.*
Chou, T. and Talalay, P. (1984) "Quantitative analysis of dose-effect relationships: the combined effects of multiple drugs or enzyme inhibitors", *Adv. Enzyme Regul.* 22, 27-55.
Cianfrocca, M. E. et al. (2006) "Phase 1 trial of the antiangiogenic peptide ATN-161 (Ac-PHSCN-NH2), a beta integrin antagonist, in patients with solid tumours", *Br. J. Cancer* 94(11), 1621-1626.
Gerlach, J. H. et al. (1986) "Multidrug resistance", *Cancer Surv.* 5(1), 25-46.
Goldie, J. H. and Coldman, A. J. (1984) "The Genetic Origin of Drug Resistance in Neoplasms: Implications for Systemic Therapy", *Cancer Res.* 44(9), 3643-3653.
Kaneda, Y. et al. (1997) "Antimetastatic effect of synthetic Glu-Ile-Leu-Asp-Val peptide derivatives containing D-amino acids", *Anti-Cancer Drugs* 8(7), 702-707.
Livant, D. L. et al. (2000) "Anti-invasive, Antitumorigenic, and Antimetastatic Activities of the PHSCN Sequence in Prostate Carcinoma", *Cancer Res.* 60(2), 309-320.
Madani, I. et al. (2008) "Does ionizing radiation stimulate cancer invasion and metastasis?", *Bull. Cancer (Montrouge)* 95(3), 292-300.
Pan, P.-S. et al. (2007) "Identification of Sansalvamide a analog potent against pancreatic cancer cell lines", *Bioorg. Med. Chem. Lett.* 17(18), 5072-5077.
Piossek, C. et al. (2003) "Potent inhibition of angiogenesis by D,L-peptides derived from vascular endothelial growth factor receptor 2", *Thromb. Haemostasis* 90(3), 501-510.
Zeng, Z. Z. et al. (2009) "α5β31 integrin ligand PHSRN induces invasion and α5 mRNA in endothelial cells to stimulate angiogenesis", *Transl. Oncol.* 2, 8-20.
Abdollahi, et al., "Inhibition of AvB3 Integrin Survival Signaling Enhances Antiangiogenic and Antitumor Effects of Radiotherapy." *Clin Cancer Res.*, 11(17):6270-6279 (2005).
Khalili, et al., "A non-RGD-based integrin binding peptide (ATN-161) blocks breast cancer growth and metastasis in vivo." *Mol Cancer Ther.*, 5(9):2271-2280 (2006).
International Search Report (ISR) mailed Sep. 17, 2010 for PCT/US2010/034497.

* cited by examiner

*Primary Examiner* — Karlheinz R Skowronek
*Assistant Examiner* — Roy Teller
(74) *Attorney, Agent, or Firm* — Medlen & Carroll, LLP

(57) ABSTRACT

Invasion-inhibiting peptides comprising either a modified cysteine (where the sulfur atom is modified with a alkyl group or other suitable group), and/or b) D-amino acids, for the treatment "cancer" in humans and animals. Such peptides can be used together with other therapies (e.g. radiation) to enhance the therapeutic benefit and reduce invasiveness.

15 Claims, 10 Drawing Sheets

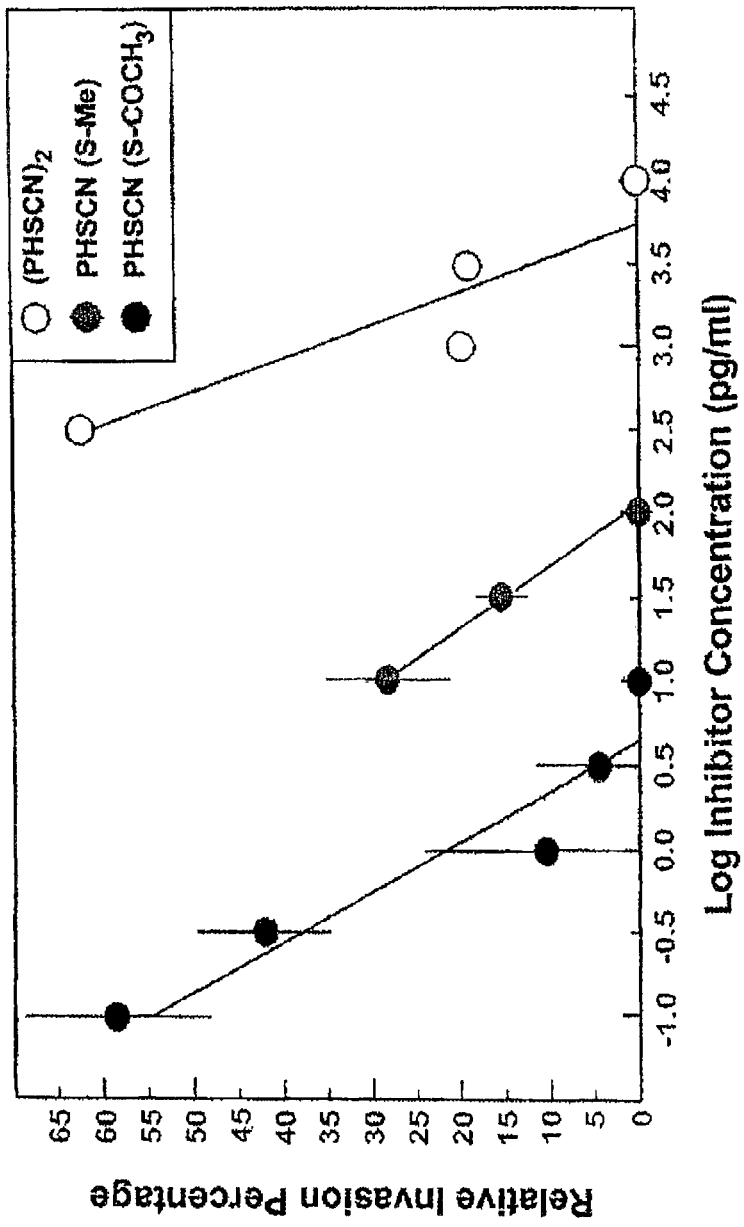
Figure 1. SUM 52 PE metastatic human breast cancer cell invasion inhibition by S-Me and S-OAc derivatives of Ac-PHSCN-NH$_2$. X axis, log inhibitor concentration in pg/ml. Y axis, mean invasion percentages, relative to serum-induced positive controls.

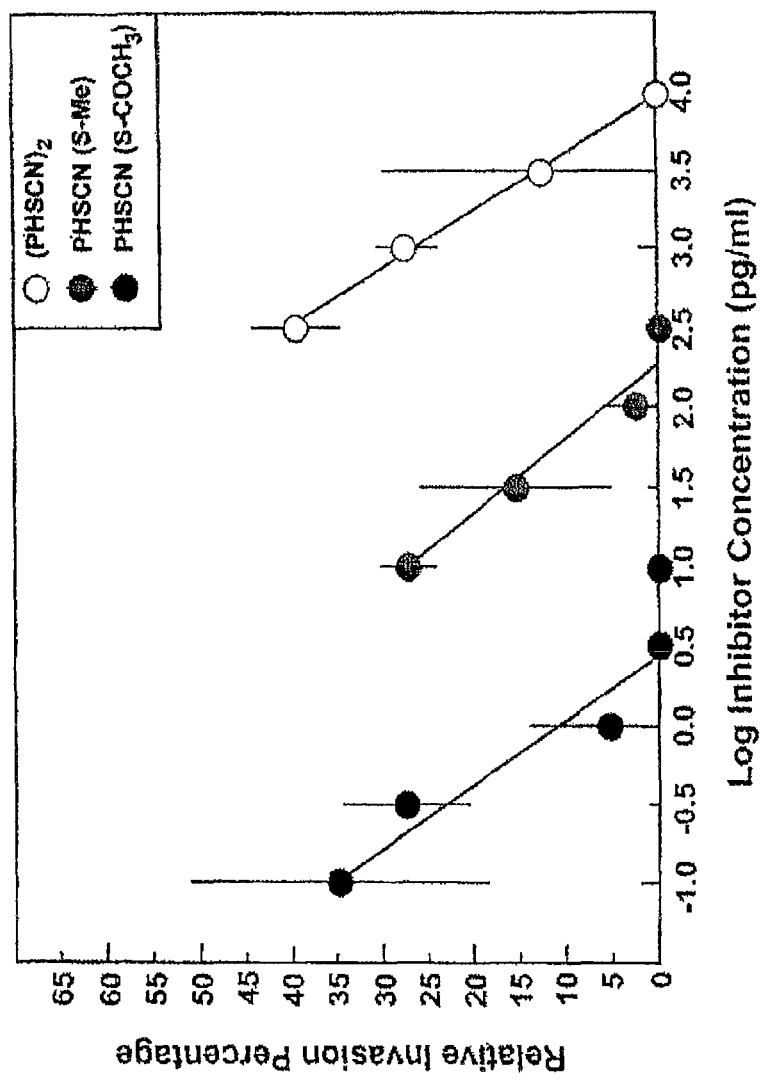
Figure 2. DU 145 metastatic human prostate cancer invasion inhibition by S-Me and S-OAc derivatives of Ac-PHSCN-NH$_2$. X axis, log inhibitor concentration in pg/ml. Y axis, mean invasion percentages, relative to serum-induced positive controls.

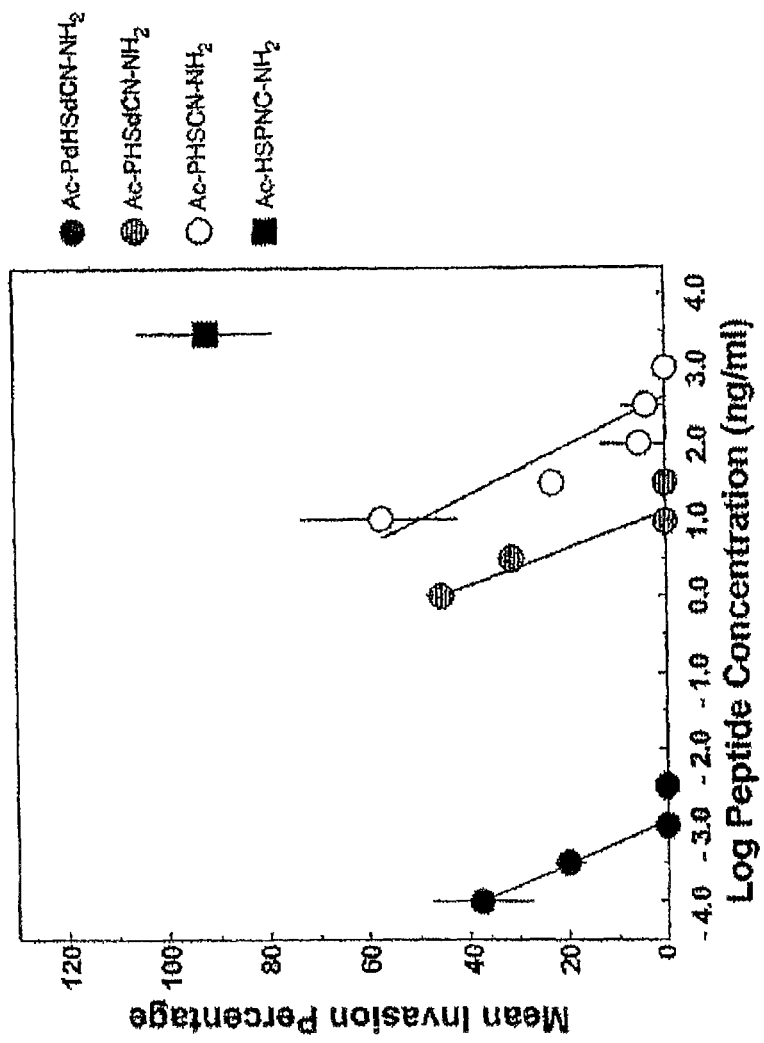

Figure 3. Potencies of Ac-PhScN-NH$_2$ and Ac-PHScN-NH$_2$ as compared to Ac-PHSCN-NH$_2$ as inhibitors of serum-induced SUM149PT metastatic human breast cancer cell invasion. X axis, log peptide concentration (ng/ml). Y-axis, mean percentages of invaded cells, relative to serum-stimulated control. Inactivity of the scrambled sequence control )Ac-HSPNC-NH$_2$ is also demonstrated.

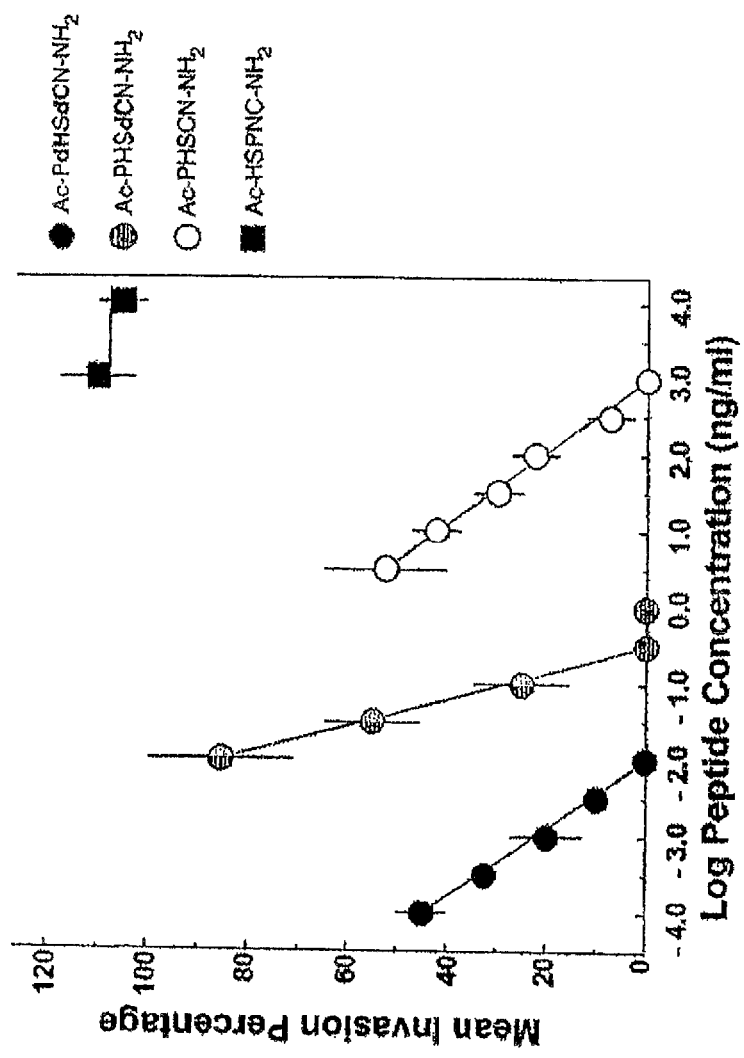

Figure 4. Potencies of Ac-PhScN-NH$_2$ and Ac-PHScN-NH$_2$, as compared to Ac-PHSCN-NH$_2$ as inhibitors of serum-induced DU 145 metastatic human prostate cancer cell invasion. X axis, log peptide concentration (ng/ml). Y-axis, mean percentages of invaded cells, relative to serum-stimulated control. Inactivity of the scrambled sequence control )Ac-HSPNC-NH$_2$ is also demonstrated.

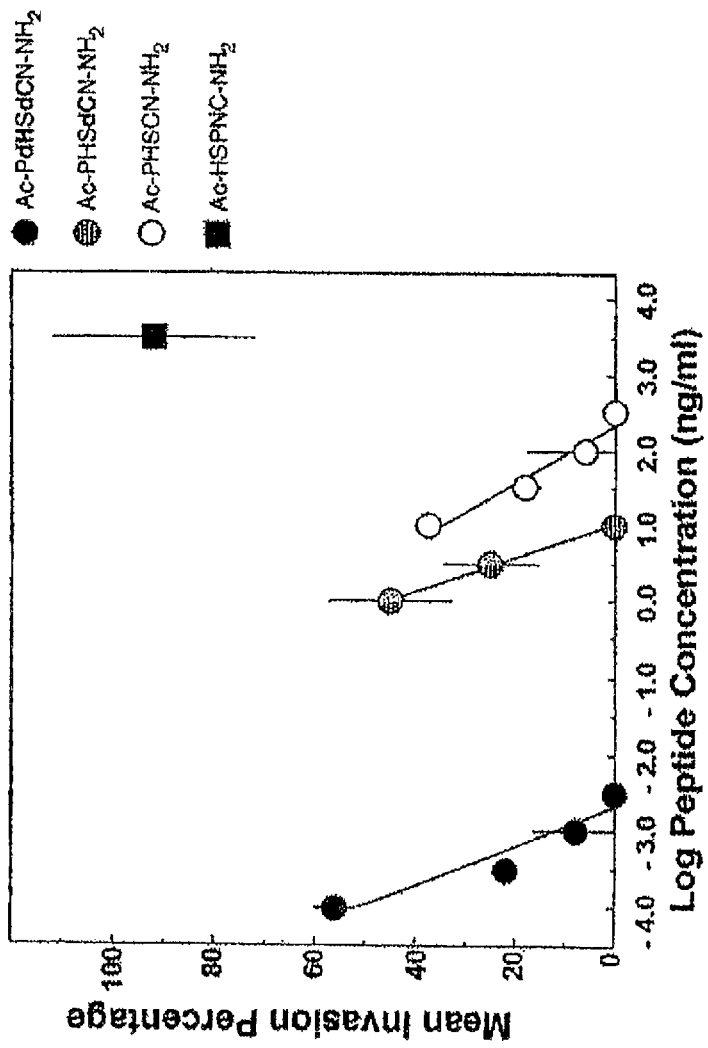

Figure 5. Potencies of Ac-PhScN-NH$_2$ and Ac-PHScN-NH$_2$, as compared to Ac-PHSCN-NH$_2$ as inhibitors of plasma fibronectin cell binding domain-induced hmvec microvascular endothelial cell invasion. X axis, log peptide concentration (ng/ml). Y-axis, mean percentages of invaded cells, relative to serum-stimulated control. Inactivity of the scrambled sequence control )Ac-HSPNC-NH$_2$ is also demonstrated.

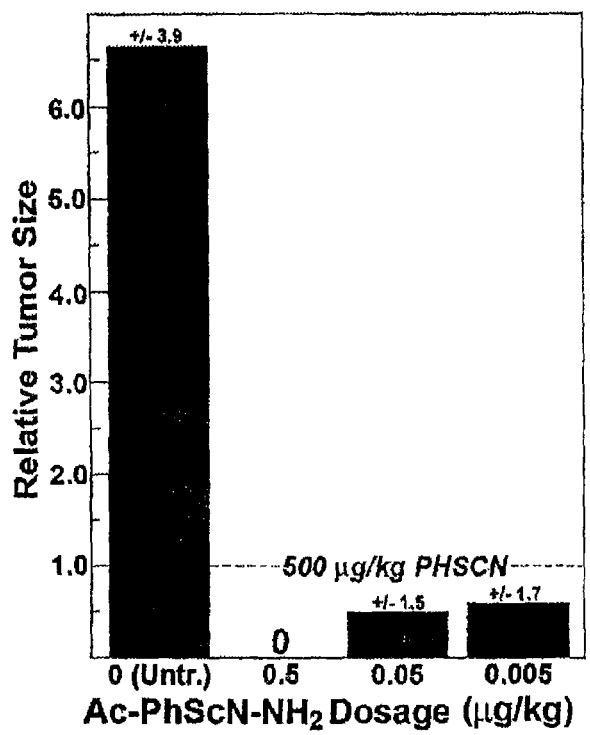
Figure 6 Effects of PhScN on DU 145 tumor growth. X-axis, PhScN dose; Y-axis, mean tumor diameters, relative to mice treated in parallel with 500 µg/kg (0.5 mg/kg) PHSCN. Means shown +/- SD.

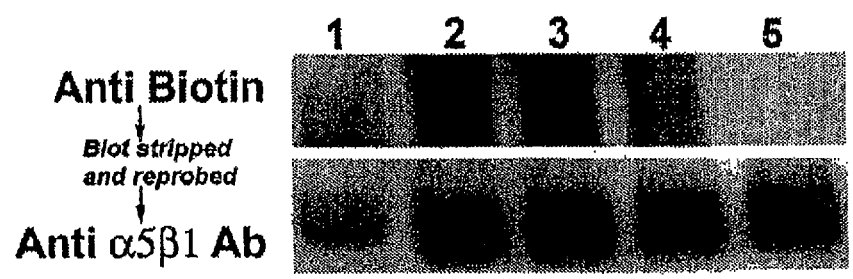
Figure 7 Binding of biotinylated PHSCN to α5 integrin in SUM149PT extracts is reduced by excess PhScN. 1, biotinylated α5β1 control, 2, ratio PhScN : PHSCN, 0:1; 3, ratio PhScN : PHSCN,1:1; 4, ratio PhScN : PHSCN, 10:1; 5, ratio PhScN : PHSCN, 50:1.

ns in size as a result of the killing of the predominant drug-sensitive cells. With the drug-sensitive cells gone, the remaining drug-resistant cells continue to multiply and eventually dominate the cell population of the tumor.

SEQUENCE LISTING

<160> NUMBER OF SEQ ID NOS: 18

<210> SEQ ID NO 1
<211> LENGTH: 5
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (4)..(4)
<223> OTHER INFORMATION: The sulfur atom of the SH group of Cysteine is
      modified with an alkyl group, an ester, an acetyl group, an
      acetoxy group, and the like
<220> FEATURE:
<221> NAME/KEY: MISC_FEATURE
<222> LOCATION: (4)..(4)
<223> OTHER INFORMATION: The sulfur atom of the SH group of Cysteine is
      modified with an alkyl group, an ester, an acetyl group, an
      acetoxy group, and the like.

<400> SEQUENCE: 1

Pro His Ser Cys Asn
1               5

```
<210> SEQ ID NO 2
<211> LENGTH: 5
<212> TYPE: PRT
<213> ORGANISM: Artificial sequence
<220> FEATURE:
<223> OTHER INFORMATION: synehtic
<220> FEATURE:
<221> NAME/KEY: MISC_FEATURE
<222> LOCATION: (1)..(1)
<223> OTHER INFORMATION: The residue in this position is an L-amino acid
      selected from the group consisting of proline, glycine, valine,
      histidine, isoleucine, phenylalanine, tyrosine, and tryptophan
<220> FEATURE:
<221> NAME/KEY: MISC_FEATURE
<222> LOCATION: (2)..(2)
<223> OTHER INFORMATION: The residue in this position is the L- or
      D-isomer of histidine
<220> FEATURE:
<221> NAME/KEY: MISC_FEATURE
<222> LOCATION: (3)..(3)
<223> OTHER INFORMATION: The residue in this position is an L-amino acid
      selected from the group consisting of serine, threonine, alanine,
      tyrosine, leucine, histidine, asparagine, and glutamine.
<220> FEATURE:
<221> NAME/KEY: MISC_FEATURE
<222> LOCATION: (4)..(4)
<223> OTHER INFORMATION: The sulfur atom of the SH group of Cysteine is
      modified.
<220> FEATURE:
<221> NAME/KEY: MISC_FEATURE
<222> LOCATION: (5)..(5)
<223> OTHER INFORMATION: The residue in this position is an L- or
      D-amino acid selected from the group consisting of asparagine,
      glutamine, serine, threonine, histidine, and tyrosine.

<400> SEQUENCE: 2

Xaa Xaa Xaa Cys Xaa
1               5

<210> SEQ ID NO 3
<211> LENGTH: 5
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: amino terminus blocked to prevent digestion by
      exopeptidases, for example by acetylation (Ac)
<220> FEATURE:
<221> NAME/KEY: MISC_FEATURE
<222> LOCATION: (4)..(4)
<223> OTHER INFORMATION: The sulfur atom of the SH group of Cysteine is
      S-methylated.
<220> FEATURE:
<221> NAME/KEY: MISC_FEATURE
<222> LOCATION: (5)..(5)
<223> OTHER INFORMATION: the carboxyl terminus blocked by standard
      methods to prevent digestion by exopeptidases, for example, by
      amidation (NH2)

<400> SEQUENCE: 3

Pro His Ser Cys Asn
1               5

<210> SEQ ID NO 4
<211> LENGTH: 5
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (1)..(1)
```

```
<223> OTHER INFORMATION: amino terminus blocked to prevent digestion by
      exopeptidases, for example by acetylation (Ac)
<220> FEATURE:
<221> NAME/KEY: MISC_FEATURE
<222> LOCATION: (4)..(4)
<223> OTHER INFORMATION: The sulfur atom of the SH group of Cysteine is
      S-acetylated.
<220> FEATURE:
<221> NAME/KEY: MISC_FEATURE
<222> LOCATION: (5)..(5)
<223> OTHER INFORMATION: the carboxyl terminus blocked by standard
      methods to prevent digestion by exopeptidases, for example, by
      amidation (NH2)

<400> SEQUENCE: 4

Pro His Ser Cys Asn
1               5

<210> SEQ ID NO 5
<211> LENGTH: 5
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (2)..(2)
<223> OTHER INFORMATION: The residue in this position is the D-isomer of
      histidine.
<220> FEATURE:
<221> NAME/KEY: MISC_FEATURE
<222> LOCATION: (4)..(4)
<223> OTHER INFORMATION: The residue in this position is the D-isomer of
      cysteine (and P, S and N are all L-isomers).

<400> SEQUENCE: 5

Pro Xaa Ser Xaa Asn
1               5

<210> SEQ ID NO 6
<211> LENGTH: 5
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: The residue in this position is an L-amino acid
      selected from the group consisting of proline, glycine, valine,
      histidine, isoleucine, phenylalanine, tyrosine, and tryptophan.
<220> FEATURE:
<221> NAME/KEY: MISC_FEATURE
<222> LOCATION: (2)..(2)
<223> OTHER INFORMATION: The residue in this position is the D-isomer of
      histidine.
<220> FEATURE:
<221> NAME/KEY: MISC_FEATURE
<222> LOCATION: (3)..(3)
<223> OTHER INFORMATION: The residue in this position is an L-amino acid
      selected from the group consisting of serine, threonine, alanine,
      tyrosine, leucine, histidine, asparagine, and glutamine.
<220> FEATURE:
<221> NAME/KEY: MISC_FEATURE
<222> LOCATION: (4)..(4)
<223> OTHER INFORMATION: The residue in this position is the D-isomer of
      cysteine or the D-isomer of homo-cysteine.
<220> FEATURE:
<221> NAME/KEY: MISC_FEATURE
<222> LOCATION: (5)..(5)
<223> OTHER INFORMATION: The residue in this position is an L- amino
      acid selected from the group consisting of asparagine, glutamine,
      serine, threonine, histidine, and tyrosine.

<400> SEQUENCE: 6
```

```
Xaa Xaa Xaa Xaa Xaa
1               5

<210> SEQ ID NO 7
<211> LENGTH: 5
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: amino terminus blocked to prevent digestion by
      exopeptidases by acetylation (Ac)
<220> FEATURE:
<221> NAME/KEY: MISC_FEATURE
<222> LOCATION: (4)..(4)
<223> OTHER INFORMATION: D-isomer of cysteine
<220> FEATURE:
<221> NAME/KEY: MISC_FEATURE
<222> LOCATION: (5)..(5)
<223> OTHER INFORMATION: the carboxyl terminus blocked by standard
      methods to prevent digestion by exopeptidases by amidation (NH2)

<400> SEQUENCE: 7

Pro His Ser Cys Asn
1               5

<210> SEQ ID NO 8
<211> LENGTH: 5
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: amino terminus blocked to prevent digestion by
      exopeptidases by acetylation (Ac)
<220> FEATURE:
<221> NAME/KEY: MISC_FEATURE
<222> LOCATION: (2)..(2)
<223> OTHER INFORMATION: D-isomer of histidine
<220> FEATURE:
<221> NAME/KEY: MISC_FEATURE
<222> LOCATION: (4)..(4)
<223> OTHER INFORMATION: D-isomer of cysteine
<220> FEATURE:
<221> NAME/KEY: MISC_FEATURE
<222> LOCATION: (5)..(5)
<223> OTHER INFORMATION: the carboxyl terminus blocked by standard
      methods to prevent digestion by exopeptidases by amidation (NH2)

<400> SEQUENCE: 8

Pro His Ser Cys Asn
1               5

<210> SEQ ID NO 9
<211> LENGTH: 8
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: amino terminus blocked to prevent digestion by
      exopeptidases by acetylation (Ac)
<220> FEATURE:
<221> NAME/KEY: MISC_FEATURE
<222> LOCATION: (4)..(4)
<223> OTHER INFORMATION: wherein the cystine at this position is
      D-Cysteine
```

```
<220> FEATURE:
<221> NAME/KEY: MISC_FEATURE
<222> LOCATION: (8)..(8)
<223> OTHER INFORMATION: the carboxyl terminus blocked by standard
      methods to prevent digestion by exopeptidases by amidation (NH2)

<400> SEQUENCE: 9

Pro His Ser Cys Asn Gly Gly Lys
1               5

<210> SEQ ID NO 10
<211> LENGTH: 8
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: amino terminus blocked to prevent digestion by
      exopeptidases by acetylation (Ac)
<220> FEATURE:
<221> NAME/KEY: MISC_FEATURE
<222> LOCATION: (2)..(2)
<223> OTHER INFORMATION: wherein the histidine at this position is
      D-histidine
<220> FEATURE:
<221> NAME/KEY: MISC_FEATURE
<222> LOCATION: (4)..(4)
<223> OTHER INFORMATION: wherein the cystine at this position is
      D-Cysteine
<220> FEATURE:
<221> NAME/KEY: MISC_FEATURE
<222> LOCATION: (8)..(8)
<223> OTHER INFORMATION: the carboxyl terminus blocked by standard
      methods to prevent digestion by exopeptidases by amidation (NH2)

<400> SEQUENCE: 10

Pro His Ser Cys Asn Gly Gly Lys
1               5

<210> SEQ ID NO 11
<211> LENGTH: 8
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: amino terminus attached to poly amidoamine
      (PAMAM) dendrimers
<220> FEATURE:
<221> NAME/KEY: MISC_FEATURE
<222> LOCATION: (5)..(5)
<223> OTHER INFORMATION: D-isomer of cysteine
<220> FEATURE:
<221> NAME/KEY: MISC_FEATURE
<222> LOCATION: (7)..(7)
<223> OTHER INFORMATION: D-isomer of histidine
<220> FEATURE:
<221> NAME/KEY: MISC_FEATURE
<222> LOCATION: (8)..(8)
<223> OTHER INFORMATION: the carboxyl terminus blocked by standard
      methods to prevent digestion by exopeptidases by amidation (NH2)

<400> SEQUENCE: 11

Lys Gly Gly Asn Cys Ser His Pro
1               5

<210> SEQ ID NO 12
<211> LENGTH: 5
<212> TYPE: PRT
```

```
<213> ORGANISM: Artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: amino terminus blocked to prevent digestion by
      exopeptidases by acetylation (Ac)
<220> FEATURE:
<221> NAME/KEY: MISC_FEATURE
<222> LOCATION: (5)..(5)
<223> OTHER INFORMATION: the carboxyl terminus blocked by standard
      methods to prevent digestion by exopeptidases by amidation (NH2)

<400> SEQUENCE: 12

Pro His Ser Cys Asn
1               5

<210> SEQ ID NO 13
<211> LENGTH: 5
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (1)..(5)
<223> OTHER INFORMATION: L-amino acid can be replace with a D-amino acid
      version at any point

<400> SEQUENCE: 13

Val Glu Gly Phe Arg
1               5

<210> SEQ ID NO 14
<211> LENGTH: 5
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: D-Glutamine
<220> FEATURE:
<221> NAME/KEY: MISC_FEATURE
<222> LOCATION: (2)..(2)
<223> OTHER INFORMATION: D-Isoleucine
<220> FEATURE:
<221> NAME/KEY: MISC_FEATURE
<222> LOCATION: (3)..(3)
<223> OTHER INFORMATION: D-leucine
<220> FEATURE:
<221> NAME/KEY: MISC_FEATURE
<222> LOCATION: (4)..(4)
<223> OTHER INFORMATION: D-aspartate
<220> FEATURE:
<221> NAME/KEY: MISC_FEATURE
<222> LOCATION: (5)..(5)
<223> OTHER INFORMATION: D-valine

<400> SEQUENCE: 14

Glu Ile Leu Asp Val
1               5

<210> SEQ ID NO 15
<211> LENGTH: 5
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
```

```
-continued

<222> LOCATION: (1)..(1)
<223> OTHER INFORMATION: amino terminus blocked to prevent digestion by
      exopeptidases by acetylation (Ac)
<220> FEATURE:
<221> NAME/KEY: MISC_FEATURE
<222> LOCATION: (5)..(5)
<223> OTHER INFORMATION: the carboxyl terminus blocked by standard
      methods to prevent digestion by exopeptidases by amidation (NH2)

<400> SEQUENCE: 15

His Ser Pro Asn Cys
1               5

<210> SEQ ID NO 16
<211> LENGTH: 8
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: amino terminus blocked to prevent digestion by
      exopeptidases by acetylation (Ac)
<220> FEATURE:
<221> NAME/KEY: MISC_FEATURE
<222> LOCATION: (2)..(2)
<223> OTHER INFORMATION: D-isomer of histidine
<220> FEATURE:
<221> NAME/KEY: MISC_FEATURE
<222> LOCATION: (4)..(4)
<223> OTHER INFORMATION: D-isomer of cysteine
<220> FEATURE:
<221> NAME/KEY: MISC_FEATURE
<222> LOCATION: (8)..(8)
<223> OTHER INFORMATION: the carboxyl terminus blocked by standard
      methods to prevent digestion by exopeptidases by amidation (NH2)
<220> FEATURE:
<221> NAME/KEY: MISC_FEATURE
<222> LOCATION: (8)..(8)
<223> OTHER INFORMATION: biotinylation of the primary amine of the
      lysine side chain

<400> SEQUENCE: 16

Pro His Ser Cys Asn Gly Gly Lys
1               5

<210> SEQ ID NO 17
<211> LENGTH: 5
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: amino terminus blocked to prevent digestion by
      exopeptidases by acetylation (Ac)
<220> FEATURE:
<221> NAME/KEY: MISC_FEATURE
<222> LOCATION: (2)..(2)
<223> OTHER INFORMATION: X is the D-isomer of histidine
<220> FEATURE:
<221> NAME/KEY: MISC_FEATURE
<222> LOCATION: (4)..(4)
<223> OTHER INFORMATION: X is the D-isomer of cysteine
<220> FEATURE:
<221> NAME/KEY: MISC_FEATURE
<222> LOCATION: (5)..(5)
<223> OTHER INFORMATION: the carboxyl terminus blocked by standard
      methods to prevent digestion by exopeptidases by amidation (NH2)

<400> SEQUENCE: 17

Pro Xaa Ser Xaa Asn
```

```
<210> SEQ ID NO 18
<211> LENGTH: 8
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: amino terminus blocked to prevent digestion by
      exopeptidases by acetylation (Ac)
<220> FEATURE:
<221> NAME/KEY: MISC_FEATURE
<222> LOCATION: (8)..(8)
<223> OTHER INFORMATION: the carboxyl terminus blocked by standard
      methods to prevent digestion by exopeptidases by amidation (NH2)
<220> FEATURE:
<221> NAME/KEY: MISC_FEATURE
<222> LOCATION: (8)..(8)
<223> OTHER INFORMATION: biotinylation of the primary amine of the
      lysine side chain

<400> SEQUENCE: 18

Pro His Ser Cys Asn Gly Gly Lys
1               5
```

COMPOUNDS FOR, AND METHODS OF, TREATING CANCER AND INHIBITING INVASION AND METASTASES

FIELD OF THE INVENTION

The invention generally relates to the treatment of cancer, and, more specifically, to compounds that inhibit the ability of cancer cells to invade tissues and cause metastases. Such compounds and methods can be used alone, or together with other anticancer therapies (including but not limited to radiation).

BACKGROUND

Success with chemotherapeutics as anticancer agents has also been hampered by the phenomenon of multiple drug resistance, resistance to a wide range of structurally unrelated cytotoxic anticancer compounds. J. H. Gerlach et al., *Cancer Surveys*, 5:25-46 (1986). The underlying cause of progressive drug resistance may be due to a small population of drug-resistant cells within the tumor (e.g., mutant cells) at the time of diagnosis. J. H. Goldie and Andrew J. Coldman, *Cancer Research*, 44:3643-3653 (1984). Treating such a tumor with a single drug first results in a remission, where the tumor shrinks in size as a result of the killing of the predominant drug-sensitive cells. With the drug-sensitive cells gone, the remaining drug-resistant cells continue to multiply and eventually dominate the cell population of the tumor.

Success treating particular cancers is also hampered by the fact that the cancer is well-advanced by the time it is diagnosed. Pancreatic cancer, colon cancer and breast cancer are good examples of the latter. Pancreatic cancer is diagnosed in almost 38,000 people in the U.S. each year, with almost 35,000 dying from the disease. In Europe the numbers are even higher, with over 60,000 diagnosed each year. Surgery is usually not practical for the majority of cases. Radiation is a contested therapy, with some researchers indicating that radiation stimulates the growth, invasion and metastases of pancreatic cancer. Chemotherapeutics, even in combination, provide only modest (weeks to months) improvements in survival. Overall, median survival from diagnosis is around 3 to 6 months; 5-year survival is less than 5%.

In sheer numbers, colon cancer is even a bigger killer. With 655,000 deaths worldwide per year, it is the third most common form of cancer and the second leading cause of cancer-related death in the Western world. When detected late, surgery may be of no use. For example, 20% of patients present with metastatic (stage 1V) colorectal cancer at the time of diagnosis, and only 25% of this group will have isolated liver metastasis that is potentially resectable. Radiation is not routinely used since it can cause radiation enteritis. Chemotherapy is often used post-surgery as adjunct therapy. However, the use of chemotherapeutics is complicated by the fact that colon cancer is often found in the elderly, who do not respond well to aggressive chemotherapy.

Breast cancer is the most common malignancy and the second leading cause of cancer death in women. In over 60% of localized breast cancer cases, histologic evidence of tumor spread to surrounding tissue is found. Patients diagnosed with invasive ductal carcinoma, the most common breast cancer, have a lower 10-year survival rate. About 30% of newly diagnosed breast cancer patients have positive lymph nodes and much poorer outcomes. Chemotherapeutics are typically employed, but acute chemotherapy-induced adverse effects are observed in most women. These include alopecia, myelosuppression, nausea, stomatitis, vomiting, neuropathy, and myalgia. Later-onset effects often include weight gain, fatigue, musculoskeletal pain, and cognitive dysfunction, especially memory loss, decreased language skills and concentration. Breast cancer chemotherapy toxicities can have severe consequences, including cardiomyopathy or secondary acute leukemia.

What is needed are better compounds and methods for treating cancer, including advanced cancer such as pancreatic cancer, colon cancer and breast cancer.

SUMMARY OF THE INVENTION

The invention generally relates to the treatment of cancer, and, more specifically, to compounds that inhibit the ability of cancer cells to invade tissues and cause metastases. Such compounds and methods can be used alone, or together with other anticancer therapies (including but not limited to radiation). In one embodiment, the present invention contemplates invasion-inhibiting chemotherapeutics for treating invasive tumors and/or advanced tumors, including but limited to advanced cancer such as pancreatic cancer, colon cancer and breast cancer. In one embodiment, the present invention contemplates chemotherapeutics which enhance the impact of radiation on cancer. In yet another embodiment, the present invention contemplates invasion-inhibiting chemotherapeutics so as to inhibit the invasion and metastases caused by radiation.

The α5β1 integrin fibronectin receptor is key to invasion by microvascular endothelial cells, an important early step in angiogenesis. Thus, the PHSCN peptide is an effective anti-invasive agent for normal human microvascular cells in vitro, as well as a potent antiangiogenic agent in vivo. In one embodiment, the anti-invasive agent is a peptide with the amino acid sequence PHSCN (SEQ ID NO:1), wherein the sulfur atom of the SH group of Cysteine is modified (e.g. with an alkyl group, an ester, an acetyl group, an acetoxy group, and the like). In one embodiment, the sulfur atom of the SH group of the cysteine residue was methylated or acetylated (S-Me or S-OAc). While not limited to any mechanism, it is believed that such modifications prevents disulfide bond formation. It is not intended that the indicated peptide be limited to just five amino acids; it may comprise the named amino acid sequence and additional amino acids added to the amino terminus (e.g. 1 to 100 additional amino acids, but typically 1 to 10), the carboxyl terminus (1-100 additional amino acids, but typically 1 to 10), or both the amino and carboxyl termini. In another embodiment, the present invention contemplates an anti-invasive agent comprising the amino acid sequence $X_1X_2X_3CX_4$ (SEQ ID NO:2), wherein the sulfur atom of the SH group of Cysteine is modified, and wherein $X_1$ is an L-amino acid selected from the group consisting of proline, glycine, valine, histidine, isoleucine, phenylalanine, tyrosine, and tryptophan, and $X_2$ is the L- or D-isomer of histidine, and $X_3$ is an L-amino acid selected from the group consisting of serine, threonine, alanine, tyrosine, leucine, histidine, asparagine, and glutamine, and $X_4$ is an L- or D-amino acid selected from the group consisting of asparagine, glutamine, serine, threonine, histidine, and tyrosine. It is also contemplated that, in some embodiments, said peptide's amino terminus is blocked with a first group, and said peptide's carboxyl terminus is blocked with a second group (where the first and second group can be the same or different), in order to render the peptide more resistant to exoproteases, e.g. the peptide (containing the modified Cysteine) is further modified with the amino terminus blocked to prevent digestion by exopeptidases, for example by acetylation (Ac); and the carboxyl terminus blocked by standard methods to prevent digestion by exopeptidases, for example, by amidation (NH$_2$). Thus, in one embodiment, S-methylated and S-acetylated derivatives of the PHSCN peptide [i.e. Ac-PHSC(S—CH$_3$)N—NH$_2$ (SEQ ID NO:3) and Ac-PHSC(S—COCH$_3$)N—NH$_2$ (SEQ ID NO:4), respectively) are contemplated. These derivatives exhibit efficacy in picomolar concentrations.

In the preferred embodiment, the anti-invasive agent is a peptide with the amino acid sequence PHSCN (SEQ ID NO:1), wherein at least two amino acids are D-isomers, and the remaining amino acids are L-isomers. In one embodiment, the D-amino acids and L-amino acids alternate. For example, in a particularly preferred embodiment, the anti-invasive agent is a peptide which has an amino acid sequence comprising PX$_1$SX$_2$N (SEQ ID NO:5), where X$_1$ is the D-isomer of histidine, and X$_2$ is the D-isomer of cysteine (and P, S and N are all L-isomers).

It is not intended that the present invention be limited to only these amino acids. In another embodiment, the present invention contemplates an anti-invasive agent comprising the amino acid sequence X$_1$X$_2$X$_3$X$_4$X$_5$ (SEQ ID NO:6), wherein X$_1$ is an L-amino acid selected from the group consisting of proline, glycine, valine, histidine, isoleucine, phenylalanine, tyrosine, and tryptophan, and X$_2$ is the D-isomer of histidine, and X$_3$ is an L-amino acid selected from the group consisting of serine, threonine, alanine, tyrosine, leucine, histidine, asparagine, and glutamine, and X$_4$ is the D-isomer of cysteine or the D-isomer of homo-cysteine, and X$_5$ is an L-amino acid selected from the group consisting of asparagine, glutamine, serine, threonine, histidine, and tyrosine.

It is also contemplated that, in some embodiments, the anti-invasive agents named above comprise a peptide wherein said peptide's amino terminus is blocked with a first group, and said peptide's carboxyl terminus is blocked with a second group (where the first and second group can be the same or different), in order to render the peptide more resistant to exoproteases, e.g. with the amino terminus blocked for example by acetylation; and the carboxyl terminus blocked by standard methods to prevent digestion by exopeptidases, for example, by amidation. Thus, in one embodiment, the present invention contemplates Ac-PHScN—NH$_2$ (SEQ ID NO:7), and Ac-PhScN—NH$_2$ (SEQ ID NO:8). These derivatives exhibit efficacy in picomolar concentrations. Moreover, in athymic nude mice, such compounds appear well-tolerated at dosages as high as 50 mg/kg.

It is further contemplated that the anti-invasive agents named above comprise the named amino acid sequence and additional amino acids added to the amino terminus (e.g. 1 to 100 additional amino acids, but typically 1 to 10), the carboxyl terminus (1-100 additional amino acids, but typically 1 to 10), or both the amino and carboxyl termini. In one embodiment, by virtue of the additional amino acids, the anti-invasive agent is up to five hundred amino acids in length. Thus, in one embodiment, the present invention contemplates an Ac-PHScNGGK—NH$_2$ peptide (SEQ ID NO:9), with D-Cysteine, as well as an Ac-PhScNGGK—NH$_2$ peptide (SEQ ID NO:10), with D-Histidine and D-Cysteine amino acids. The GGK spacer is useful (among other things) for conjugation to poly amidoamine (PAMAM) dendrimers to develop multivalent PAMAM-(KGGNcShP-Ac)$_x$ conjugates (SEQ ID NO:11). While not limiting the invention in any way to a mechanism, it is believed that the combination of high peptide potency and the multiplicity of peptide display achieved using PAMAM carriers will allow for multivalent interaction with $\alpha_5\beta_1$ integrin receptors thus producing a significantly enhanced anti-invasive and anti-metastatic activity. Furthermore, the use of PAMAM dendrimers as carriers allows the conjugation of chemotherapeutic agents, imaging probes, and/or radioisotopes, which opens the door for combination therapy on a single, water-soluble, compact, nano-carrier. The proposed nano-conjugates can be exploited for treatment of other types of solid tumors.

In one embodiment, the present invention provides a method of treating cancer comprising: a) providing: i) a subject having cancer, and ii) a composition of matter comprising a peptide which has an amino acid sequence comprising PX$_1$SX$_2$N (SEQ ID NO:5), where X$_1$ is the D-isomer of histidine, and X$_2$ is the D-isomer of cysteine; and b) administering said composition to said subject. In one embodiment, the peptide is Ac-PX$_1$SX$_2$N—NH$_2$ (SEQ ID NO:17), where X$_1$ is the D-isomer of histidine, and X$_2$ is the D-isomer of cysteine. The present invention further contemplates administering such a peptide before and/or after surgical removal of the primary tumor. In one embodiment, the method comprises administering such a peptide as adjunct therapy with additional chemotherapeutics (e.g. combination therapy).

The present invention further contemplates administering such a peptide before and/or after radiation. Thus, in one embodiment, the present invention provides a method of treating cancer comprising: a) providing: i) a subject having cancer, ii) a source of radiation, and iii) a composition of matter comprising a peptide which has an amino acid sequence comprising PX$_1$SX$_2$N (SEQ ID NO:5), where X$_1$ is the D-isomer of histidine, and X$_2$ is the D-isomer of cysteine; b) administering said composition to said subject; and c) irradiating said cancer with said radiation source. In one embodiment, the peptide is Ac-PX$_1$SX$_2$N—NH$_2$ (SEQ ID NO:17), where X$_1$ is the D-isomer of histidine, and X$_2$ is the D-isomer of cysteine. In one embodiment, the method further comprises d) administering said composition to said subject after said irradiating.

It is not intended that the present invention be limited to treatment of the primary tumor or to treatment where metastatic disease has been confirmed. In one embodiment, the primary tumor is removed surgically and the peptides of the present invention are used to prevent or inhibit metastases to other organs. By way of a non-limiting example, metastasis to the lung, resulting in pulmonary insufficiency, is a major life-threatening consequence of metastatic breast cancer. Indeed, sometimes the lung is the site at which the first recurrence of breast cancer is found. Therefore, the present invention contemplates embodiments where metastases have been found (acute treatment), as well as where metastases have not yet been detected, but where it is desired that they be inhibited or prevented (prophylactic treatment).

Thus, in one embodiment, the present invention provides a method of treating cancer comprising: a) providing: i) a subject who has been treated surgically to remove a primary tumor, and ii) a composition of matter comprising a peptide which has an amino acid sequence comprising PX$_1$SX$_2$N (SEQ ID NO:5), where X$_1$ is the D-isomer of histidine, and X$_2$ is the D-isomer of cysteine; and b) administering said composition to said subject. In one embodiment, the peptide is Ac-PX$_1$SX$_2$N—NH$_2$ (SEQ ID NO:17), where X$_1$ is the D-isomer of histidine, and X$_2$ is the D-isomer of cysteine. In one embodiment, metastatic disease has been detected in said subject. In another embodiment, metastatic disease has not been detected in said subject.

In one embodiment, the peptides of the present invention (described herein) are used for imaging or to detect the spread of cancer in vivo, or for histologic examination in vivo or in vitro. Thus, in one embodiment, the present invention contemplates that the peptides of the present invention are labeled (e.g. with radiolabels, fluorescent labels, and the like).

In one embodiment, the Ac-PhScN—NH$_2$ peptide (SEQ ID NO:8) is labeled or "tagged" for histologic analysis with biotin. While not limited to any precise chemistry, such labeling can be conveniently done with the addition of GGK to the C-terminus, followed by biotinylation of the primary amine of the lysine side chain (Ac-PhScNGGK(-Bio)-NH$_2$ (SEQ ID NO:16).

Thus, in one embodiment, the present invention provides a method of imaging (or detecting) cancer (or the metastases thereof) comprising: a) providing: i) a subject having cancer (or suspected of having cancer), and ii) a composition of matter comprising a labeled peptide which has an amino acid sequence comprising PX$_1$SX$_2$N (SEQ ID NO:5), where X$_1$ is the D-isomer of histidine, and X$_2$ is the D-isomer of cysteine; and b) administering said composition to said subject. In one embodiment, the peptide is Ac-PX$_1$SX$_2$N—NH$_2$ (SEQ ID NO:17), where X$_1$ is the D-isomer of histidine, and X$_2$ is the D-isomer of cysteine, and wherein the label is selected from the group consisting of biotin, a fluorescent label, and a radiolabel.

DESCRIPTION OF THE FIGURES

FIG. 1 is a plot showing the quantitated invasion-inhibiting potencies of S-methylated and S-acetylated derivatives of the PHSCN peptide [i.e. Ac-PHSC(S—CH$_3$)N—NH$_2$ (SEQ ID NO:3) and Ac-PHSC(S—COCH$_3$)N—NH$_2$ (SEQ ID NO:4), respectively] based on an in vitro invasion assay utilizing metastatic human breast cancer cells.

FIG. 2 is a plot showing the quantitated invasion-inhibiting potencies of S-methylated and S-acetylated derivatives of the PHSCN peptide [i.e. Ac-PHSC(S—CH$_3$)N—NH$_2$ (SEQ ID NO:3) and Ac-PHSC(S—COCH$_3$)N—NH$_2$ (SEQ ID NO:4), respectively] based on an in vitro invasion assay utilizing metastatic human prostate cancer cells.

FIG. 3 is a plot showing the quantitated invasion-inhibiting potencies of Ac-PHScN—NH$_2$ (SEQ ID NO:7), and Ac-PhScN—NH$_2$ (SEQ ID NO:8), in comparison with Ac-PHSCN—NH$_2$ (SEQ ID NO:12) as well as a scrambled peptide Ac-HSPNC—NH$_2$ (SEQ ID NO:15), based on an in vitro invasion assay utilizing metastatic human breast cancer cells.

FIG. 4 is a plot showing the quantitated invasion-inhibiting potencies of Ac-PHScN—NH$_2$ (SEQ ID NO:7), and Ac-PhScN—NH$_2$ (SEQ ID NO:8), in comparison with Ac-PHSCN—NH$_2$ (SEQ ID NO:12) as well as a scrambled peptide Ac-HSPNC—NH$_2$ (SEQ ID NO:15), based on an in vitro invasion assay utilizing metastatic human prostate cancer cells.

FIG. 5 is a plot showing the quantitated invasion-inhibiting potencies of Ac-PHScN—NH$_2$ (SEQ ID NO:7), and Ac-PhScN—NH$_2$ (SEQ ID NO:8), in comparison with Ac-PHSCN—NH$_2$ (SEQ ID NO:12) as well as a scrambled peptide Ac-HSPNC—NH$_2$ (SEQ ID NO:15), based on an in vitro invasion assay utilizing microvascular endothelial cells.

FIG. 6 is a bar graph comparing the antitumorigenic effects of systemic in vivo Ac-PhScN—NH$_2$ (SEQ ID NO:8) therapy at three different dosages (0.5, 0.05, and 0.005 micrograms per kg) with the antitumorigenic effects of 0.5 mg (500 micrograms) per kg of Ac-PHSCN—NH$_2$ (SEQ ID NO:12) therapy using the DU 145 prostate cancer (as well as with untreated controls).

FIG. 7 is a blot showing the binding of biotinylated PHSCN to α5β1 integrin in breast cancer cell extracts, and that excess unlabeled PhScN peptide can competitively remove biotinylated PHSCN.

DEFINITIONS

Figure 8:
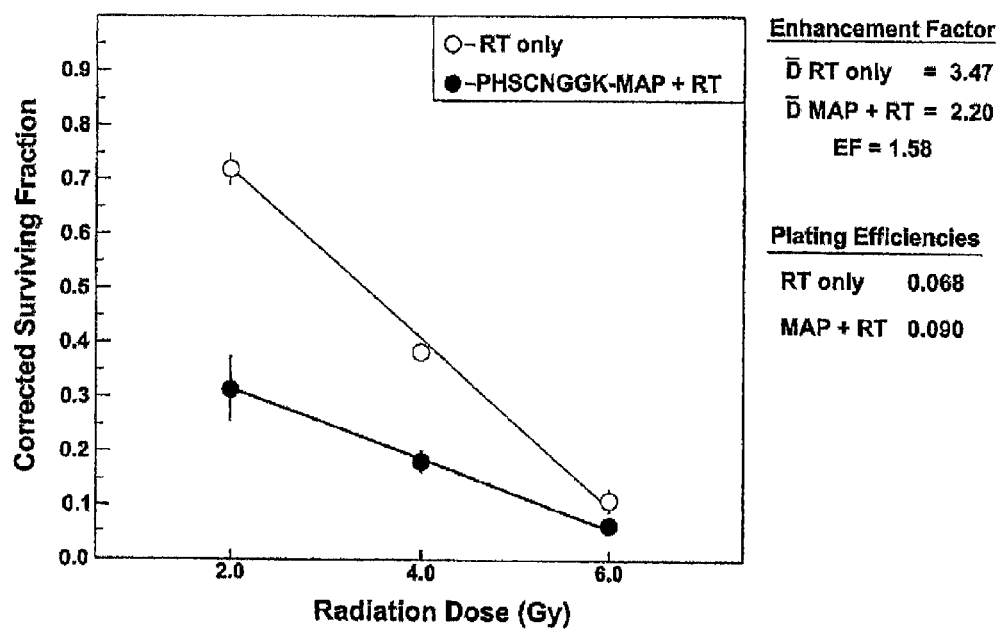
FIG. 8 is a plot showing that cancer cells treated with an invasion-inhibiting peptide are more sensitive to radiation.

The present invention contemplates using a) invasion-inhibiting peptides comprising a modified cysteine (as described herein), and/or b) D-amino acid containing invasion-inhibiting peptides, for the treatment "cancer" in humans and animals. As used herein, malignant neoplasia are referred to as "cancer" and characterized by tumor cells which typically will ultimately metastasize into distinct organs or tissues. Malignant neoplasia include solid and hematological tumors, and the present invention contemplates treating them both. "Solid tumors" are exemplified by tumors of the breast, bladder, bone, brain, central and peripheral nervous system, cervix, colon, endocrine glands (e.g. thyroid and adrenal cortex), esophagus, endometrium, germ cells, head and neck, kidney, liver, lung, larynx and hypopharynx, mesothelioma, ovary, pancreas, prostate, rectum, renal, sarcoma, skin (e.g. melanoma), small intestine, stomach (or gastric cancer), soft tissue, testis, ureter, vagina and vulva. Malignant neoplasias include inherited cancers exemplified by Retinoblastoma and Wilms tumor. In addition, malignant neoplasia include primary tumors in said organs and corresponding secondary tumors in distant organs ("tumor metastases"). Hematological tumors are exemplified by aggressive and indolent forms of leukemia and lymphoma, namely non-Hodgkins disease, chronic and acute myeloid leukemia (CML/AML), acute lymphoblastic leukemia (ALL), Hodgkins disease, multiple myeloma and T-cell lymphoma. Also included are myelodysplastic syndrome, plasma cell neoplasia, paraneoplastic syndromes, cancers of unknown primary site as well as AIDS related malignancies (e.g. Kaposi's sarcoma).

It must be stressed that, as used herein, "cancer" does not necessarily require the formation of metastases in distant organs, and includes certain tumors which exert devastating effects on the primary organ itself through their aggressive growth properties. These can lead to the destruction of the tissue and organ structure finally resulting in failure of the assigned organ function (e.g. failure of the liver, kidney, etc.).

Drug resistance is of particular importance for the frequent failure of standard cancer therapeutics. In one embodiment, the present invention contemplates treating cancer that has become "drug resistant."

In some cases a tumor that cannot be completely removed by surgery (an "unresectable cancer"). The present invention contemplates, in one embodiment, treating unresectable cancer (including but not limited to unresectable pancreatic cancer, and liver cancer) with the D-amino acid-containing peptides described herein.

"Invasion-inhibiting peptides" inhibit cancer cells in vitro and in vivo from invading basement membranes and other tissues, respectively. However, this term is used as a convenient term for identifying one function of such peptides, and not intended to be limiting in any manner. For example, data in the examples show that certain D-amino acid containing peptides of the present invention do more than inhibit invasion and appear to eliminate (depending on the concentration) the presence of cancer in vivo, even if administered after the cancer had progressed to the point that it was palpable. Moreover, the term "peptide" is used even though the compound contains D-amino acids or is otherwise modified. In one embodiment, the present invention contemplates, for example, cyclic versions of the D-amino acid-containing peptides described above, in which the necessary conformation for binding is stabilized by nonpeptides, using methods described in U.S. Pat. No. 5,192,746 to Lobl, et al., U.S. Pat. No. 5,169,862 to Burke, Jr., et al., U.S. Pat. No. 5,539,085 to Bischoff, et al., U.S. Pat. No. 5,576,423 to Aversa, et al., U.S. Pat. No. 5,051,448 to Shashoua, and U.S. Pat. No. 5,559,103 to Gaeta, et al., all hereby incorporated by reference.

In some embodiments, the present invention contemplates utilizing a) invasion-inhibiting peptides comprising a modified cysteine (as described herein), and/or b) D-amino acid containing invasion-inhibiting peptides, in "combination therapy" or as "adjunct therapy." As used herein, these terms are used to indicate that the peptides can be used before, after or together with some other type of therapy or therapies, including but not limited to surgery, radiation, and chemotherapy. Examples of known chemotherapeutic anti-cancer agents frequently used for combination therapy include, but not are limited to (i) alkylating/carbamylating agents such as Cyclophosphamid, Ifosfamid, Thiotepa, Melphalan, or chloroethylnitrosourea (BCNU); (ii) platinum derivatives like cisplatin, oxaliplatin or carboplatin; (iii) antimitotic agents/tubulin inhibitors such as vinca alkaloids (vincristine, vinblastine, vinorelbine), taxanes such as Taxol, Taxotere and analogs as well as new formulations and conjugates thereof; (iv) topoisomerase inhibitors such as anthracyclines such as Doxorubicin, epipodophyllo-toxines (such as Etoposide) and camptothecin analogs such as Topotecan; (v) pyrimidine antagonists such as 5-fluorouracil (5-FU), Capeditabine, Arabinosylcytosine/Cytarabin or Gemcitabine; (vi) purin antagonists such as 6-mercaptopurine, 6-thioguanine or fludarabine, and (vii) folic acid antagonists such as methotrexate and pemetrexed.

Other classes of agents contemplates in the context of combination therapy include but are not limited to (i) kinase inhibitors such as e.g. Glivec, ZD-1839/Iressa, Bay43-9006, SU11248 or OSI-774/Tarceva; (ii) proteasome inhibitors such as PS-341; (iii) histone deacetylase inhibitors like SAHA, PXD101, MS275, MGCD0103, Depsipeptide/FK228, NVP-LBH589, Valproic acid (VPA) and butyrates; (iv) heat shock protein inhibitors like 17-allylaminogeldanamycin (17-MG); (v) vascular targeting agents (VAT) and anti-angiogenic drugs like the VEGF antibody Avastin or the KDR tyrosine kinase inhibitor PTK787/ZK222584; (vi) monoclonal antibodies such as Herceptin or MabThera/Rituxan or C225/Erbitux as well as mutants and conjugates of monoclonal antibodies and antibody fragments; (vii) oligonucleotide based therapeutics like G-3139/Genasense; (viii) protease inhibitors (ix) hormonal therapeutics such as antiestrogens (e.g. Tamoxifen), anti-androgens (e.g. Flutamide or Casodex), LHRH analogs (e.g. Leuprolide, Goserelin or Triptorelin) and aromatase inhibitors.

Still other known anti-cancer agents which can be used for combination therapy include bleomycin, retinoids such as all-trans retinoic acid (ATRA), DNA methyltransferase inhibitors such as the 2-deoxycytidine derivative Decitabine, alanosine, cytokines such as interleukin-2 or interferons such as interferon-gamma, TRAIL, DR4/5 agonistic antibodies, FasL- and TNF-R agonists.

As used herein, the peptides (whether alone or in combination with other anti-cancer agents) are "administered" or "delivered" or "introduced" to the human or animal in any of the generally accepted modes of administration available in the art. Illustrative examples of suitable modes of administration include intravenous, oral, nasal, parenteral, topical, transdermal and rectal delivery. Oral and intravenous delivery are preferred. However, for skin cancer, topical administration may be preferred.

In some embodiments, administration is made directly to the tumor site such as with a "drug eluting implant" or by "intratumoral injection." For the latter procedure, image guidance (CT scan, for example) is used to place a hollow needle into the tumor. The peptides of the present invention can then be injected directly into the tumor. In one embodiment, the present invention contemplates combination therapy that is intratumoral. For example, the peptides of the present invention can be used in combination with gene therapy (e.g. an adenovirus containing p53) that is administered intratumorally. Non-limiting examples of drug eluting devices for implantation include implants as described in U.S. Pat. Nos. 3,993,073 and 5,660,848, hereby incorporated by reference. Drug eluting devices can also be placed remote from the tumor site.

The present invention contemplates treating all "stages" of cancer. The "stage" of a cancer is a descriptor (usually numbers I to IV) of how much the cancer has grown and spread (e.g. whether it has spread to distant organs).

It is not intended that the present invention be limited by the dose or duration of treatment, or the stage of the cancer. In one non-limiting example, the present invention contemplates an embodiment whereby the human or animal is administered a peptide of the present invention thrice-weekly, at relatively low dosage levels (e.g. 0.5 to 50 ug/kg) in order to prevent metastatic disease progression (and, ideally, to inhibit growth) in a wide variety of end-stage human cancers, without significant adverse events.

It is not intended that the present invention be limited to "curing" or "eliminating" cancer. Significant extension of life is also contemplated (e.g. by inhibiting or retarding growth and invasion), even if the subject (e.g. human or animal) ultimately succumbs to the cancer.

It is also not intended that the present invention be limited to only one type of peptide for the treatment of any one subject. For example, where the cancer in the subject for any reason becomes unresponsive or resistant (after a period of time of treatment) to one of the peptides described herein, the treatment can proceed to a different peptide. For example, in one embodiment, where the subject is first treated with a D-amino acid containing invasion-inhibiting peptide and the efficacy of the treatment appears to be declining (e.g. due to the formation of antibody by the subject), the present invention contemplates using a second peptide, such as an invasion-inhibiting peptide comprising a modified cysteine (as described herein) (which is unlikely to bind with high affinity to the subjects antibody due to the bulky substituent which is attached to the sulfur atom of the cysteine). By changing peptides, one may achieve a greater extension of life.

DESCRIPTION OF THE INVENTION

The PHSCN (SEQ ID NO:1) peptide, in the form of Ac-PHSCN—NH$_2$ (where all the amino acids are L-isomers) (SEQ ID NO:12), was developed in the late 1990s and targets α5β1 in vivo to inhibit α5β1-mediated, pFn-dependent invasion and metastatic disease progression. Systemic Ac-PHSCN—NH$_2$ (SEQ ID NO:12) prevents metastatic disease progression in animal models by human breast and prostate cancer cell lines, at concentrations of 1 to 2 μM or dosages of 0.5 to 50 mg/kg. Livant et al., "Anti-invasive, antitumorigenic, and antimetastatic activities of the PHSCN sequence in prostate carcinoma," *Cancer Res.* 60: 309-320 (2000). It is equally potent at preventing α5β1-mediated invasion by hmvec, normal human microvascular cells, which is believed to be an important early step in angiogenesis. Zeng et al., Transl One 2(1):8-20 (2009). Since α5β1 integrin is expressed at high levels on tumors and associated blood vessels, it is viewed as an important therapeutic target in cancer. Based on these results, the PHSCN peptide (SEQ ID NO:1) was commercially licensed as an anticancer agent. Testing revealed that it was a potent antitumorigenic agent in a variety of animal models of metastatic cancer. Following these studies, the PHSCN peptide (SEQ ID NO:1) entered Phase 1 clinical trial. Thrice-weekly, systemic administration of PHSCN (SEQ ID NO:1) monotherapy at modest dosage levels prevented metastatic disease progression in a wide variety of end-stage human cancers for 4 to 14 months, without significant adverse events. Cianfrocca et al., "Phase 1 trial of the antiangiogenic peptide ATN-161 (Ac-PHSCN—NH$_2$) (SEQ ID NO:12), a beta integrin antagonist, in patients with solid tumours," Br. J. Cancer 94: 1621-1626 (2006). Thus it was very well tolerated, and appeared to be efficacious for significant periods of time. Eventually, however, all patients became resistant to the therapy and succumbed to their disease.

To improve on these results, two strategies were employed. First, the SH group on the cysteine was modified in order to prevent it from being involved in a putative disulfide bond (discussed more below). Second, D-amino acids were employed as substitutes for L-amino acids.

A. Modifying the SH Group of Cysteine

It has been proposed that invasion inhibition by PHSCN (SEQ ID NO; 1) depends on disulfide (S—S) bond formation with the α5β1 receptor. We tested this hypothesis directly by assaying the invasion-inhibitory activities of two PHSCN peptide (SEQ ID NO:1) derivatives incapable of S—S bond formation, where the sulfur atom of the SH group of the cysteine residue was methylated or acetylated (S-Me or S-OAc). As shown in our results (see Example 1, below), S-Me and S-OAc derivatives of the PHSCN peptide are many orders of magnitude more potent as invasion inhibitors in vitro, suggesting that S—S bond formation with α5β1 is actually an undesirable side reaction.

S-Me and S-OAc derivatives may be endoproteinase-sensitive, albeit possibly not as sensitive as the parental PHSCN peptide (SEQ ID NO:1). It is possible that some groups (e.g. bulky groups) may sterically block proteases. Thus, other modifications of the SH group of cysteine are contemplated. For example, the present invention contemplates embodiments wherein the SH group is modified with groups selected from the group consisting of alkyl, aryl, alkanediyl, alkynyl, arenediyl, aralkyl, heteroarenediyl, heteroaralkyl, heteroaryl, alkenyl, alkenediyl, alkynediyl, acyl, alkylidene, or a substituted version of any of these groups, preferably where the number of carbons is ≤20, more typically ≤12 carbons, more preferably ≤10 carbons or ≤8, or between 2 and 6 carbons.

B. Introducing D-Amino Acids

The present invention contemplates embodiments wherein the PHSCN peptide (or variants thereof) comprises two or more D-amino acids. In one embodiment, D-amino acids and L-amino acids alternate. For example, in one embodiment, the present invention contemplates the Ac-PhScN—NH$_2$ peptide (SEQ ID NO:8) (wherein the D-isomers for histidine and cysteine are employed rather than the L-isomers). It has been empirically found to be orders of magnitude more potent than Ac-PHSCN—NH$_2$ (SEQ ID NO:12) (containing all L-amino acids), which gave promising results in Phase 1 clinical trial (wherein all of the amino acids were L-isomers), both as an invasion inhibitor in vitro and as an inhibitor of tumorigenesis in vivo. Without limiting the invention to any particular mechanism (indeed, an understanding of mechanism is unnecessary for the successful use of such peptides), it is possible that Ac-PhScN—NH$_2$ (SEQ ID NO:8) is far more potent invasion inhibitor than Ac-PHSCN—NH$_2$ (SEQ ID NO:12) for two reasons: 1) resistance to digestion by endoproteinases, and 2) prevention of disulfide bond formation after binding to α5β1 integrin.

With regard to proteases, since all amino acids in mammalian proteins are L stereoisomers, proteinases have evolved to degrade proteins formed from L-amino acids only. Thus, the Ac-PhScN—NH$_2$ (SEQ ID NO:8) peptide will likely be very resistant to degradation by endoproteinases, often present at high levels in tumors and increasing with malignancy. Thus, by replacing histidine and cysteine with their D-stereoisomers to prevent disulfide bond formation, we also may achieve (hopefully total) endoproteinase resistance.

Peptides containing D-amino acid substitutions have been shown to be more stable. For example, substitution of a D-amino acid in somatostatin-related peptides increased endoproteinase resistance, thereby increasing half-life in animal studies. However, the impact of D-amino acid substitutions on potency and efficacy must be empirically determined. For example, a peptide from the binding site of the VEGF receptor, VEGFR-2 (SEQ ID NO:13), containing 4 D-amino acid substitutions, was 10-fold more potent at inhibiting VEGF binding than the wildtype peptide. Piossek et al., "Potent inhibition of angiogenesis by D,L-peptides derived from vascular endothelial growth factor receptor 2," Thromb Haemost 90: 501-510 (2003). Also, sansalvamide peptides with a single D-amino acid substitution were more potent growth inhibitors for pancreatic and colon cancer cell lines in vitro. Pan et al. "Identification of sansalvamide a analog potent against pancreatic cancer cell lines," Bioorg. & Medicinal Chem. Lett. 17: 5072-507732, 33 (2007). However, attempts to significantly increase the antimetastatic potency of the fibronectin-related peptide, Glu-Ile-Leu-Asp-Val (EILDV) (SEQ ID NO:14), with D-amino acids were not successful. In this regard, researchers synthesized various EILDV-related peptides substituted with a D-amino acid. EILDV containing D-Glu or D-Ile inhibited cell adhesion and migration as potently as EILDV, whereas replacing Leu, Asp or Val with the corresponding D-isomer reduced the antiadhesive activities. The inhibitory effect of EILDV-related peptides containing D-Leu, D-Asp or D-Val on migration was also lower than that of EILDV (SEQ ID NO; 14). All synthetic EILDV-related peptides containing D-amino acids inhibited metastasis by B16-BL6 melanoma cells to the same extent as EILDV, whereas the specific activity of EILDV was decreased by the D-amino acid substitution. The researchers cautioned that the results indicate one must find a balance of stability and biological activity. Kaneda et al., "Antimetastatic effect of synthetic Glu-Ile-Leu-Asp-Val peptide derivatives containing D-amino acids. Anti-cancer drugs 8(7):702-7 (1997). In sum, such reports indicate one may pay a price in efficacy in order to get better stability. Thus, it is surprising that the D-amino acid peptides described herein have such markedly improved efficacy.

C. Radiation Sensitizer

Tumor treatment via the use of ionizing radiation can be enhanced by increasing the radiosensitivity of the tumor cells. In one embodiment, the present invention contemplates utilizing the peptides of the present invention to enhance radiosensitivity.

The ideal radiation sensitizer should reach the tumor in adequate concentrations and act selectively in the tumor compared with normal tissue. It should have predictable pharmacokinetics for timing with radiation treatment and could be administered with every radiation treatment. The ideal radiation sensitizer should have minimal toxicity itself and minimal or manageable enhancement of radiation toxicity. It is believed that the above-described D-amino acid-containing peptides (as well as the peptides with modified cysteine) satisfy these demands since it is safe and non-toxic, and targets a specific ligand.

The subject with cancer can be given such a peptide systemically (e.g. by intravenous administration) or locally (e.g. by intratumoral injection or implant) prior to radiation. It is not intended that the present invention be limited by the particular timing or dosing. In one non-limiting example, the present invention contemplates an embodiment whereby the human or animal is administered a peptide of the present invention at relatively low dosage levels (e.g. 0.5 to 50 ug/kg) between 10 minutes and 3 hours prior to radiation. Administration of one of the invasion-inhibiting peptides described herein together with radiation provides enhanced tumor cell killing and thus an advantage in the treatment of human malignancies. Importantly, the combination therapy allows for a lower dose of irradiation, i.e. 2 Gy or 4 Gy instead of 6 Gy.

It is not necessary that the mechanism for making tumors more sensitive to radiation be known, in order to practice the invention successfully. It is believed, however, that because the $\alpha 5\beta 1$ fibronection receptor supports survival, as well as mediating invasion, administration of a highly potent derivative of the PHSCN peptide, such as the Ac-PhScN—$NH_2$ peptide may render tumor cells and the endothelial cells of their associated vasculature more sensitive to radiation therapy (keeping in mind that both tumor cells and the microvascular endothelial cells of their associated vasculature express high levels of activated $\alpha 5\beta 1$ integrin fibronectin receptors). This could either increase the efficacy of standard dosage and fractionation schedules, or allow for reduced dosage levels and/or fraction numbers.

Radiation is cytotoxic to both tumor cells and cells of the surrounding normal tissues. This lack of specificity is a major limitation to the use of radiotherapy. For example, radiotherapy of prostate cancer can result in acute and late complications due to toxicities to the rectum, including rectal bleeding. Radiotherapy of prostate cancer can also cause early and late toxicities to the genitourinary tract. Anorexia, nausea, and fatigue are also very common complaints during gastric radiation therapy. The dose-limiting organs for irradiation of pancreatic cancer include small intestine, stomach, liver, kidneys, and spinal cord. Dose limiting tissue injuries in radiation therapy for liver cancer include liver, stomach, duodenum, bowels, and kidneys. Acute complications include fatigue, transient elevation of liver function test, nausea, vomiting, and fever. Late complications include hepatic failure, radiation pneumonitis, and gastrointestinal bleeding. The most frequent complications associated with irradiation of breast cancer include arm and breast edema. When lung tissue is included in the radiation field, breast irradiation can significantly increase the incidence of symptomatic pneumonitis. Radiation-induced toxic effects in lung cancer include pneumonitis, which peaks in 2 months and is usually resolved in a year. Lung fibrosis often occurs a few months after radiation therapy, and becomes chronic. Radiation-induced sequelae in brain cancer are usually irreversible and progressive. They include thrombus formation, neurocognitive damage, and radiation necrosis.

Combining systemic PhScN therapy with radiotherapy may thus have several desirable effects. It may increase the therapeutic efficacy of the radiotherapy without added toxic effects to enhance the efficacy of a standard dosage schedule. By increasing the therapeutic efficacy of radiotherapy, the addition of systemic PhScN may also allow for reduced dosage levels and/or fewer fractions of radiation to be administered. This would reduce the damaging effects of radiation on normal tissues surrounding the tumor, such as those summarized above.

D. Inhibiting Invasiveness Caused by Irradiation

Experiments with cells in culture and with animal tumors have shown that IR stimulates invasion and metastasis and activates pro-invasive and prometastatic cellular activities through upregulation of key molecules. Mandani et al. *Bull. Cancer* 2008 March; 95(3):292-300. Importantly, the invasion-inhibiting peptides of the present invention can block this radiation-induced invasiveness. Thus, in one embodiment, the present invention contemplates administering such peptides before, during or after radiation. Where the potential for any particular cancer to be stimulated by radiation to invade and metastasize is not known, administering the invasion-inhibiting peptides before, during or after radiation can be viewed as preventative treatment. On the other hand, the present invention also contemplates, in one embodiment, screening a tumor in vitro (e.g. using a basement membrane assay as shown in the examples below) for its potential to be stimulated by radiation to invade and metastasize, and then administering the invasion-inhibiting peptides before, during or after radiation in those instances where the in vitro screen demonstrates the cancer can be stimulated by radiation to invade and metastasize.

EXPERIMENTAL

Some of the examples below employ an invasion assay utilizing naturally occurring basement membranes from 72 hour sea urchin embryos. Breast and prostate cancer invasion was induced with serum; hmvec invasion was induced with the PHSRN sequence of the plasma fibronectin (pFn) cell binding domain. The assay is described in U.S. Pat. No. 6,001,965, hereby incorporated by reference.

Example 1

In this example, PHSCN peptides, where the sulfur of the SH group of cysteine was modified to block disulfide bond formation, were tested in an in vitro invasion assay utilizing naturally occurring basement membranes. More specifically, the invasion-inhibiting potencies of S-methylated and S-acetylated derivatives of the PHSCN (SEQ ID NO:1) peptide [i.e. Ac-PHSC(S—$CH_3$)N—$NH_2$ (SEQ ID NO:3) and Ac-PHSC(S—$COCH_3$)N—$NH_2$, (SEQ ID NO:4), respectively] were quantitated [in comparison with PHSCN (SEQ ID NO:1) dimerized by S—S bond formation] with two types of metastatic human cancer cell lines, i.e. a breast cell line (SUM 52 PE) and a prostate cell line (DU 145) (see FIG. 1 and FIG. 2, respectively). These modified peptides prevent breast cancer and prostate cancer invasion at concentrations in the pg/ml range. The S-methylated variant appears to be 1000-fold more potent, and S-acetylated variant appears to be 100,000-fold more potent, than the unmodified PHSCN (SEQ ID NO:1).

Example 2

In this example, PHSCN peptides, where two L-amino acids are substituted with D-amino acids, were tested in an in vitro invasion assay utilizing naturally occurring basement membranes. More specifically, the invasion-inhibiting potencies of Ac-PHScN—NH$_2$ (SEQ ID NO:7), and Ac-PhScN—NH$_2$ (SEQ ID NO:8) were quantitated [in comparison with Ac-PHSCN—NH$_2$ (SEQ ID NO:12) as well as a scrambled peptide Ac-HSPNC—NH$_2$ (SEQ ID NO:15)] with two types of metastatic human cancer cell lines, i.e. a breast cell line (SUM 52 PE) and a prostate cell line (DU 145) (see FIG. 3 and FIG. 4, respectively), as well as human microvascular cells ("hmvec") (see FIG. 5). These modified peptides prevent breast cancer and prostate cancer invasion at concentrations in the pg/ml range. Indeed, the peptide comprising two D-amino acids, Ac-PhScN—NH$_2$ (SEQ ID NO:8), demonstrated inhibition in the range of 3 to 10 pg/ml (5.0 to 16.7 pM). The peptide comprising only one D-amino acid was also better than the controls, albeit not as potent as the two D-amino acid-containing peptide.

Table I compares IC$_{50}$'s of Ac-PHSCN—NH$_2$ ("PHSCN") (SEQ ID NO:12), Ac-PhScN—NH$_2$ (SEQ ID NO:8) ("PhScN"), Ac-PHScN—NH$_2$ (SEQ ID NO:7) ("PHScN"), and the S-methylated and S-acetylated PHSCN derivatives [Ac-PHSC(S-Me)N—NH$_2$ (SEQ ID NO:3) and Ac-PHSC(S—COCH$_3$)N—NH$_2$ (SEQ ID NO:4)]. The IC$_{50}$ for PhScN is over 10,000-fold lower than that for PHSCN. Similar decreases in IC$_{50}$ were obtained for PHSC(S-Me)N and PHSC(S—COCH$_3$)N, suggesting that prevention of S—S bond formation with the target α5β1 is key for increased potency.

Example 3

In this example, PHSCN peptides, where two L-amino acids are substituted with D-amino acids, were tested in vivo. FIG. 6 compares the antitumorigenic effects of systemic Ac-PhScN—NH$_2$ (SEQ ID NO:8) therapy at three different dosages (0.5, 0.05, and 0.005 micrograms per kg) with the antitumorigenic effects of 0.5 mg (500 micrograms) per kg of Ac-PHSCN—NH$_2$ (SEQ ID NO:12) therapy using the DU 145 prostate cancer (as well as with untreated controls). The experiment involved generating subcutaneous DU 145 tumors in nude mice. More specifically, 500,000 suspended DU 145 cells were injected subcutaneously into the flanks of athymic nude mice. All mice were allowed to grow untreated DU 145 tumors in their flanks for about 8 weeks. All 3 therapies (i.e. using the three different dosages) were administered thrice-weekly by tail vein injection after the tumors became palpable. Each treatment group consisted of 8 intramuscular (flank) tumors. After 7 weeks of treatment, when the untreated tumors were very large, all mice were sacrificed at the same time, and all tumors dissected out and measured. The results show that, relative to the mean diameter of the 8 PHSCN-treated tumors, the 8 untreated tumors were over 6-fold larger.

Importantly, no tumor tissue was visible in any of the mice treated with 0.5 μg/kg Ac-PhScN—NH$_2$ (SEQ ID NO:8). This indicates that the D-amino acid containing peptide is doing more than just inhibiting invasion and growth. It would appear that, at that particular concentration, the peptide is causing cell death. While it is not necessary for the successful practice of the invention to understand the mechanism, it may be that the peptide is causing apoptosis of cancer cells.

Example 4

In this experiment, biotinylated PHSCN peptide (Ac-PHSCNGGK(Bio)-NH$_2$) (SEQ ID NO:18) was mixed with varying amounts of unlabeled Ac-PhScN—NH$_2$ (SEQ ID NO:8). The mixed peptides were bound to detergent extracts of SUM149PT cells. A denaturing, non-reducing gel was run, blotted, and reacted with anti biotin primary antibody (FIG. 7). PhScN:PHSCN ratios were 0:1, 1:1, 10:1, or 50:1, as shown in lanes 2-5, respectively. Lane 1 contains the biotinylated α5β1 control. After probing with anti biotin antibody, the blot was stripped and reprobed with anti α5β1 antiserum as the primary antibody to demonstrate equal loading. As shown by the progressively reduced signal in the anti biotin blot, PhScN is an efficient competitor for PHSCN binding to the α5 integrin subunit. Thus, it is likely to interact with the same target site on α5 integrin as the PHSCN peptide. Alternatively PhScN binding could produce a structural or conformational change in the α5 subunit, such as a change in disulfide bonding pattern, that prevents binding of biotinylated PHSCN.

Example 5

In this example, evidence for the peptides of the present invention being useful as radiation sensitizers is presented. DU 145 prostate cancer cells were preincubated with 20 ug per ml Ac-PHSCNGGK-MAP (multiantigenic peptide dendrimer) for one hour, and then irradiated. After irradiation alone (control), or PHSCNGGK-dendrimer treatment followed by irradiation, cells were trypsinized, counted, and plated at clonal densities. There was no dendrimer present after clonal plating. Fourteen days later, cells were fixed and stained with crystal violet. Colony counting was done using an automated counter. The median effective radiation dose (MED) (see Chou and Talalay, Adv Enzyme Regul 1984; 22:27-55) was calculated for control and radiation with PHSCNGGK-dendrimer, and the enhancement ratio was calculated as the MED in the control curve divided by the MED in the or irradiation curve (FIG. 8). The enhancement ratio, which is larger than one, is consistent with radiosensitization. The dendrimer concentration used is non-toxic by itself, as reflected by the plating efficiencies not being much different between the two samples, as shown. While this experiment did not involve peptides with D-amino acids (or with modified Cysteine residues), the activity of the "parent" peptide, given the other data provided herein, suggests that D-amino acid variants (or variants with modified Cysteine residues) will also provide radiosensitization.

Example 6

In this example, two pancreatic cancer cell lines were tested under conditions which demonstrate that radiation causes these cancer cells to be more invasive. Adherent BxPC-3 and Panc1 cells were irradiated. Panc1 cells received a single 2 Gy dose. BxPC-3 cells received a single 3 Gy dose. Approximately 45 minutes later, the cells were suspended (trypsinized), pelleted and resuspended in medium containing 10% fetal calf serum. Then, the appropriate concentration of the Ac-PHSCN—NH$_2$ (SEQ ID NO: 12) peptide, as well as a scrambled peptide Ac-HSPNC—NH$_2$ (SEQ ID NO:15), was added to the suspended cells to make a final peptide concentration of 1 μg/ml, and they were dropped onto the surfaces of SU-ECM (sea urchin embryo basement membranes). At the time the cells were placed on the basement membranes, one hour had elapsed since irradiation. Cells were incubated on the basement membranes for 16 hours at 37° C. in 5% CO$_2$, prior to scoring at 400-fold magnification, under phase contrast optics. All single cells adherent to the basement membranes were scored, with respect to whether they were inside the basement membranes (invaded), or were still adherent to the exterior surface (uninvaded). Mean invasion percentages were determined with their first standard deviations for each sample.

Figure 9:
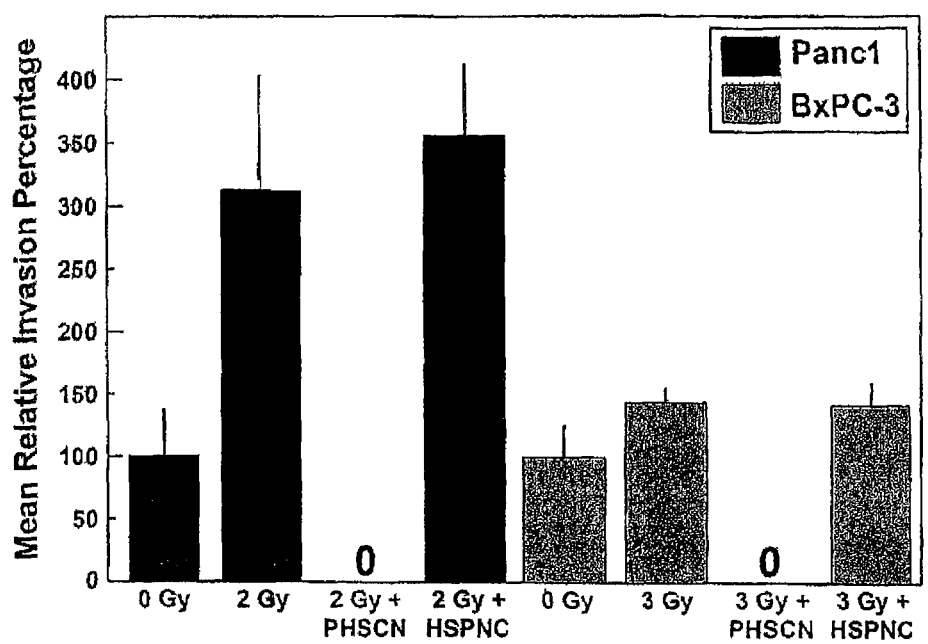
FIG. 9 is a bar graph demonstrating that some cancer cells become dramatically more invasive after exposure to radiation, and that this invasiveness can be reduced dramatically with an invasion-inhibiting peptide.

The results are shown in a bar graph (FIG. 9). Looking at the first two bars, it is clear that radiation increases the invasiveness of Panc1 cells dramatically (while the impact of radiation is not as dramatic with BxPC-3 cells). However, in both instances, the presence of the invasion-inhibiting peptide reduced invasion to zero (which the scrambled peptide demonstrated no inhibition of invasiveness).

Example 7

In this example, antibodies are used to measure downregulation of surface α5β1 levels on irradiated pancreatic cancer cells. Cells were prebound to 1 μg per ml Ac-PHSCN—NH$_2$ (SEQ ID NO:12) peptide per 20,000 cells in medium containing 10% fetal bovine serum for serum for 1 hour at 37° C. The peptide-containing medium was removed, and replaced with serum-containing medium, prior to irradiation. Adherent cells were irradiated once: 2 Gy for Panc1 cells, and 3 Gy for BxPC-3 cells. One hour after irradiation, cells were quickly rinsed with phosphate-buffered saline (PBS) pH 7.4), then fixed for 15 minutes in 4% Paraformaldahyde (commercially available from Fluka) in PBS at room temperature. After three complete washes of PBS at 5 min intervals, the fixed cells were blocked with 10% NGS (Normal Goat Serum, commercially available from Vector) in PBS and 0.2% Triton X-100, for 1 h to reduce the background staining. After blocking, medium containing NGS was removed, and replaced with medium containing primary antibody and 10% fetal calf serum. Cells were incubated directly in the primary antibody (affinity-purified P1D6 mouse monoclonal anti α5β1 antibody, MAb1969, commercially available from Chemicon, Inc.) diluted 1:500. Incubation was in 5% NGS in PBS and Triton overnight at 4° C. Then, the cells were washed to remove the primary antibody. After three PBS washes, cells were incubated in anti-mouse IgG secondary antibody, conjugated with fluorosceine isothiocyanate (FITC) fluorescence marker (commercially available from Jackson ImmunoResearch Lab, Inc) at 1:200 dilution for 1 h at room temperature. After 3 to 5 rinses in PBS, slides were mounted with Vectashield Mounting medium, treated with DAPI (4',6-Diamidino-2-phenylindole), sealed with nail polish, and then examined under 400-fold magnification, with a Zeiss Scanning laser Confocal Microscope (LSM510).

Figure 10:
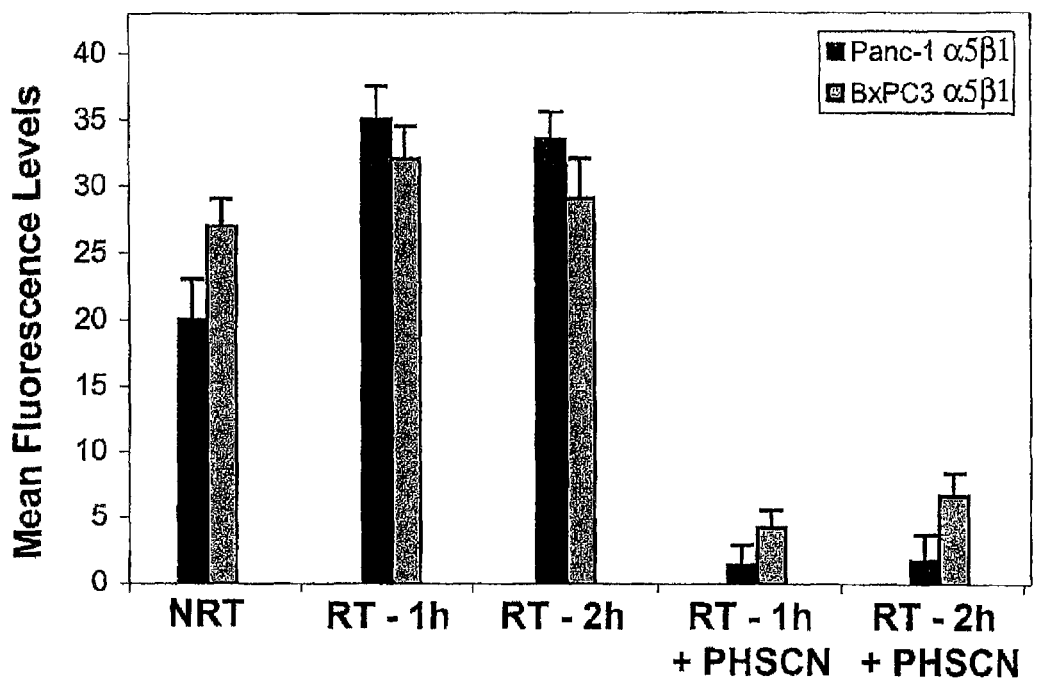
FIG. 10 is a bar graph showing down regulation of surface α5β1 integrin on irradiated cancer cells by an invasion-inhibiting peptide.

Means and first standard deviations (SD) were calculated using Image-Pro Plus software over 30 areas per treatment selected randomly under 400-fold magnification, then copied and pasted on Microsoft Excel data sheets for further data analysis. All data (see FIG. 10) are expressed as mean±SD and evaluated with ANOVA Student t-test. Significance was set at P<0.05. It is clear that the expression of α5β1 is higher on the irradiated cancer cells (both for the 1 hr and 2 hr) relative to expression on cancer cells that received no irradiation ("NRT"). Exposure to the invasion-inhibiting peptide dramatically downregulated α5β1 expression (both for the 1 hr and 2 hr treated cells).

From the above, it should be clear that the present invention provides a method of treating a wide variety of tumor types, and in particular, treating invasive tumors. With these potent inhibitors (now provided by the present invention), the physician is able to change and/or optimize therapy, including combining therapies.

TABLE 1

IC50's in pg/ml for 7 PHSCN derivatives.

| PEPTIDE | S—S | IC$_{50}$ (pg/ml) |
| --- | --- | --- |
| PHSCN | yes | 30,000 |
| PHSCNGGK-MAP (8) | yes | 300 |
| (PHSCN)$_2$ | yes | 100-500 |
| PHSC(S—CH$_3$)N | no | 1 |
| PHSC(S—COCH$_3$)N | no | 0.1 |
| PHScN | ? | 5 |
| PhScN | ? | 0.3 |

S—S, indicates derivatives capable of forming disulfide (S—S) bonds with each other or with their integrin target.
IC50 denotes the concentrations exhibiting a 50% inhibition of invasion, relative to stimulated controls.

The invention claimed is:

1. A composition, comprising a peptide which has an amino acid sequence consisting of $PX_1SX_2N$ (SEQ ID NO:5), where $X_1$ is the D-isomer of histidine, and $X_2$ is the D-isomer of cysteine, and P, S and N are all L-isomers.

2. The composition of claim 1, wherein said peptide's amino terminus is blocked with a first group, and said peptide's carboxyl terminus is blocked with a second group, in order to render the peptide more resistant to exoproteases.

3. The composition of claim 2, wherein said resistant peptide consists of Ac-PhScN—$NH_2$ (SEQ ID NO:8).

4. A composition of claim 3, wherein said peptide linked to a dendrimer.

5. The composition of claim 4, wherein said peptide is linked via a GGK spacer to a polyamidoamine (PAMAM) dendrimer.

6. The composition of claim 4, wherein said dendrimer is multivalent.

7. A method of treating cancer comprising: a) providing: i) a subject having cancer, and ii) a composition of claim 1; and b) administering said composition to said subject.

8. The method of claim 7, wherein said subject has a primary tumor, and said administering of step b) is after surgical removal of the primary tumor.

9. The method of claim 7, wherein the method comprises administering said peptide as adjunct therapy with at least one additional chemotherapeutic.

10. The method of claim 7, wherein said cancer is irradiated prior to said administering of step b).

11. The method of claim 7, wherein said cancer is irradiated after said administering of step b).

12. The method of claim 7, wherein said administering is intravenous.

13. The method of claim 7, wherein said cancer is selected from the group consisting of pancreatic cancer, prostate cancer, colon cancer, lung cancer, kidney cancer, breast cancer and melanoma.

14. The method of claim 9, wherein said additional chemotherapeutic is Taxol.

15. The method of claim 9, wherein said additional chemotherapeutic is Taxotere.

* * * * *